(12) United States Patent
Kim et al.

(10) Patent No.: US 6,222,060 B1
(45) Date of Patent: Apr. 24, 2001

(54) PROCESS FOR PREPARING O-(CARBOALKOXY) PHENYLMETHANESULFONYL CHLORIDE DERIVATIVES

(75) Inventors: Dae Whang Kim; Young Kwan Ko; Dong Wan Koo; Hae Sung Chang; Jae Wook Ryu; Jae Chun Woo, all of Daejeon (KR)

(73) Assignee: Korean Research Institute of Chemical Technology (KR)

( * ) Notice: Subject to any disclaimer, the term of this patent is extended or adjusted under 35 U.S.C. 154(b) by 0 days.

(21) Appl. No.: 09/509,440

(22) Filed: Mar. 28, 2000

(30) Foreign Application Priority Data

Sep. 30, 1997 (KR) .................................................. 97/50282
Sep. 30, 1997 (KR) .................................................. 97/50283
Sep. 30, 1997 (KR) .................................................. 97/50284

(51) Int. Cl.$^7$ ................................................ C07C 309/58
(52) U.S. Cl. ............................................................. 560/14
(58) Field of Search ................................. 560/14; 568/28

(56) References Cited

U.S. PATENT DOCUMENTS

| | | | |
|---|---|---|---|
| 2,667,503 | * | 1/1954 | Senn . |
| 2,778,852 | | 1/1957 | Adam et al. . |
| 2,888,486 | * | 5/1959 | Gregory . |
| 4,042,600 | * | 8/1977 | DiPippo . |
| 4,191,702 | * | 3/1980 | Chapelet et al. . |
| 4,393,211 | * | 7/1983 | Tonne et al. ..................... 546/153 |
| 4,420,325 | | 12/1983 | Sauers . |
| 4,689,425 | | 8/1987 | Kachhy et al. . |
| 4,764,309 | | 8/1988 | Decker et al. . |
| 5,504,249 | | 4/1996 | Isak et al. . |

FOREIGN PATENT DOCUMENTS 234249   1/1987   (EP) .
413264   8/1990   (EP) .

OTHER PUBLICATIONS

CA:125:196382 abs of WO9619493, Jun. 1996.*
CA:111:97282 abs of DE3517844, Mar. 1986.*
CA:109:124410 abs of 4678500, Jul. 1987.*
CA:97:144033 abs of Indian J Chem Sect A by Das et al 21A (7) pp 723–725, 1982.*
Chem. Abstract Vo. 114, 1991 (re Hauxue Shiijie 31 211 (1990) (CA 114,101,765).

* cited by examiner

*Primary Examiner*—Jean F. Vollano
(74) *Attorney, Agent, or Firm*—Finnegan, Henderson, Farabow, Garrett & Dunner

(57) ABSTRACT

A process for preparing an o-(carboalkoxy) phenylmethanesulfonyl chloride derivative of formula (1),

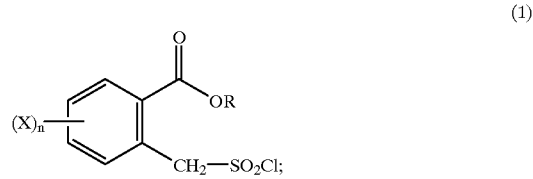

(1)

wherein:

X is chosen from a hydrogen atom, halogen atoms, $C_1$ to $C_6$ alkyl groups, $C_1$ to $C_6$ haloalkyl groups, $C_1$ to $C_6$ alkoxy groups, $C_1$ to $C_6$ alkoxycarbonyl groups, a nitro group, and a phenyl group;

R is chosen from $C_1$ to $C_6$ alkyl groups, $C_1$ to $C_6$ haloalkyl groups, and $C_3$ to $C_6$ cycloalkyl groups; and n is chosen from integers ranging from 1 to 4, is discussed.

13 Claims, No Drawings

PROCESS FOR PREPARING O-(CARBOALKOXY) PHENYLMETHANESULFONYL CHLORIDE DERIVATIVES

This application is the national phase of PCT/KR98/00302, filed Sep. 30, 1998, now WO99/16743.

BACKGROUND OF THE INVENTION

1. Field of the Invention

The present invention relates to a process for preparing o-(carboalkoxy)phenylmethanesulfonyl chloride derivatives and more particularly, to a novel process for preparing o-(carboalkoxy)phenylmethanesulfonyl chloride expressed by the following formula 1, having a lactone compound as a starting material which is cyclic ester compound, and o-(chloromethyl)benzoyl chloride, o-(chloromethyl)benzoic acid ester derivatives and o-(carboalkoxy)phenyl methanethiosulfonic acid salt as intermediates, which is an important compound for the synthesis of sulfonyl urea herbicide.

(1)

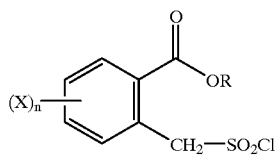

wherein:

X represents hydrogen; halogen; $C_1$~$C_6$ alkyl group; $C_1$~$C_6$ halloalkyl group; $C_1$~$C_6$ alkoxy group; $C_1$~$C_6$ alkoxycarbonyl group; nitro group; or phenyl group;

R represents $C_1$~$C_6$ alkyl group; $C_1$~$C_6$ halloalkyl group; or $C_3$~$C_6$ cycloalkyl group;

n represents 1 to 4 as number of substituents.

2. Description of the Prior Art

The o-(carboalkoxy)phenylmethanesulfonyl chloride derivatives, represented as the above formula 1, are described as essential raw materials for synthesis of sulfonyl urea herbicide (U.S. Pat. No. 4,420,325 and Germany Publishment No. 3,927,788).

The conventional process for synthesizing o-(carboalkoxy)phenylmethanesulfonyl chloride derivatives expressed by the formula 1 has been reported in the U.S. Pat. No. 4,420,325 and Hauxue Shijie 31 211(1990)(CA 114 101, 765). The process is summarized in the following Scheme 1.

Scheme 1

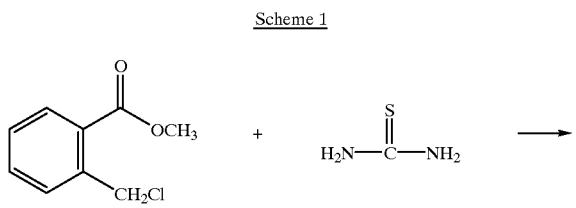

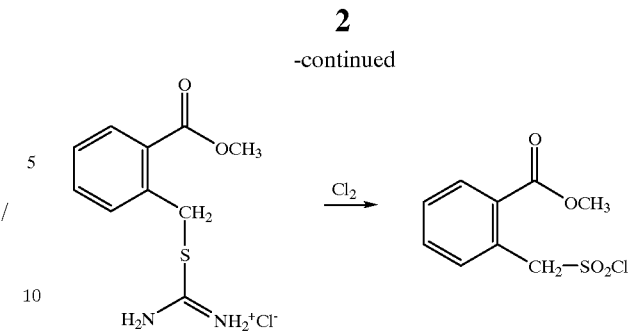

According to the conventional process of the above Scheme 1, o-(chloromethyl)benzoic acid methyl ester and thiourea are reacted for the synthesis of isothiouronium salt as an intermediate and then, the intermediate is chlorinated to prepare phenylmethanesulfonyl chloride as a final product. However, in light of the fact that thiourea designed for the synthesis of isothiouronium salt is a potential carcinogenic material, its industrial application on a mass scale is not easily made available.

Further, the method for preparing the o-(chloromethyl)benzoic acid methyl ester, used as a starting material in Scheme 1, is disclosed in some patent specifications. For example, he methyl group of side chain of the o-methylbenzoic acid methyl ester is chlorinated by reaction of chlorine and hydrogen chloride gas, simultaneously with UV radiation, as described by U.S. Pat. No. 4,689,425. However, this method has generated a lot of by-products, in spite of the fact that the reaction is terminated at the 10% level to the remaining initial substance. Thus, the method has a difficulty in purifying a final product, let alone a low yield.

Also, according to another method of preparing o-(chloromethyl)benzoyl chloride, described in U.S. Pat. No. 5,504,249, phthalide and thionyl chloride are reacted in the presence of an organic nitrogen compound and hydrogen chloride catalyst at 160~170° C., thereby obtaining the final compound. However, this method has recognized some disadvantages in that the reaction is not easily made available in a conventional reactor due to the boiling point of the thionyl chloride and hydrogen chloride at 79° C. and −85° C., respectively. Thus, the method may not easily be applied to the industrial process.

Another methods for preparing chlorine-substituted carboxylic acid chloride via reaction between a lactone compound with phosgen has been disclosed; hence, a catalyst includes pyridine(U.S. Pat. No. 2,778,852), quaternary ammonium salt(U.S. Pat. No. 4,764,309) or phosphine oxide (EP Patent No. 413, 264). However, these methods have some disadvantages in that the reaction should be performed using phosgen having a boiling point 8° C. at more than 120° C. Furthermore, since phosgen is very toxic, the process is very dangerous in its gaseous state.

To overcome the above shortcomings, the inventor et al. have endeavored to develop a preparing process useful for the industrial mass production of a compound expressed by the formula 1.

SUMMARY OF THE INVENTION

Therefore, the object of the present invention is to provide a novel process for preparing o-(carboalkoxy) phenylmethanesulfonyl chloride derivatives expressed by the formula 1, wherein it comprises:

A lactone compound, a cyclic ester compound, is reacted with thionyl chloride($SOCl_2$) in the presence of Lewis acid and quaternary-ammonium salt catalyst to prepare carbonyl chloride compounds in a high yield at a lower temperature;

An alcohol compound, a reacting material and solvent, is reacted with the above intermediate compound, so prepared, for esterification in an easier procedure and under a mild condition, thus preparing o-(chloromethyl)benzoic acid ester derivatives;

The reacting mixture is further reacted with less-toxic thiosulfonic acid salt instead of using thiourea having carcinogenic potential, followed by chlorination to obtain o-(carboalkoxy)phenylmethanesulfonyl chloride derivatives as a final product expressed by the formula 1.

DETAILED DESCRIPTION OF THE INVENTION

The present invention relates to a process for preparing o-(carboalkoxy)phenylmetlhanesulfonyl chloride derivatives, wherein it comprises:

a) A lactone compound of the following formula 2 is reacted with thionyl chloride($SOCl_2$) in the presence of Lewis acid and quaternary-ammonium salt catalyst to prepare a o-(chloromethyl)benzoyl chloride of the following formula 3;

b) A compound of the above formula 3 is esterified in alcohol compound as a reacting material and solvent to prepare a o-(chloromethyl)benzoic acid ester derivatives of the following formula 4;

c) A compound of the above formula 4 is reacted with thiosulfonic acid salt to prepare a o-(carboalkoxy) phenylmethanethiosulfonic acid salt of a following formula 5; and d) A compound of the above formula 5 is chlorinated to prepare a o-(carboalkoxy)phenylmethanesulfonyl chloride derivative of the following formula 1.

(2)
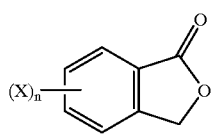

(3)
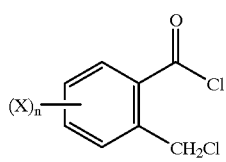

(4)
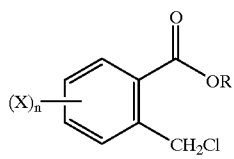

(5)
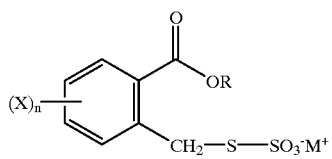

-continued (1)
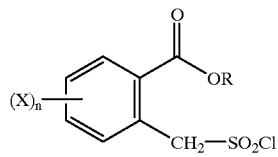

wherein:

X represents hydrogen, halogen, $C_1$~$C_6$ alkyl group, $C_1$~$C_6$ halloalkyl group, $C_1$~$C_6$ alkoxy group, $C_1$~$C_6$ alkoxycarbonyl group, nitro group or phenyl group;

R represents $C_1$~$C_6$ alkyl group, $C_1$~$C_6$ halloalkyl group or $C_3$~$C_6$ cycloalkyl group;

n represents an integer of 1 to 4 as number of substituents.

The present invention is explained in more detail as set forth hereunder.

A process for preparing carbonyl chloride from lactone compounds according to the invention is explained as set forth hereunder.

The above reaction is carried out at 80~120° C., preferably 90~100° C. If the reaction temperature is lower than 80° C., the reaction is not well performed but in case of exceeding more than 120° C., by-products may occur.

And both Lewis acid and quaternary-ammonium salt are employed as reaction catalyst. The commonly used Lewis acids include $MgCl_2$, $MgBr_2$, $SnCl_2$, $SnCl_4$, $TiCl_4$, $AlCl_3$, $FeCl_3$, $BF_3 \cdot Et_2O$, $BCl_3$, $B(OEt)_3$, $B(OMe)_3$, $B(O—iPr)_3$ and it is preferred to use boron-based Lewis acid. The detailed examples of quaternary-ammonium salts used for the reaction include halide of aliphatic alkylammonium or aromatic alkylammonium for example, tetramethylammnonium chloride, tetraethylammonium chloride, tetrabutylammonium chloride, benzyltrimethyl ammonium chloride, benzyltriethylammonium chloride and benzyltributylammonium chloride. Even though there is no restriction on the contents of catalyst, the content of Lewis acid for a latone compound is in the range of 0.1~20 mol %, more preferably in the range of 0.5~5 mol %; that of ammonium salt is in the range of 0.1~20 mol %, more preferably in the range of 0.5~5 mol %.

Further, the content of thionyl chloride for a lactone compound as a reacting material is in the molar ratio of 1~10 equivalent, more preferably in the molar ratio of 1~2 equivalent.

With the above conditions, the reaction is generally carried out at atmospheric pressure. According to this invention, the reaction is carried out without solvent but when a solvent needs to be used, inert organic solvents (e.g., toluene, xylene, chlorobanzene, dichlorobenzene), which does not affect the reaction, is employed. After the reaction is completed, a desired compound of the formula 3 is recovered in a common purification method.

Moreover, the method of preparing o-(chloromethyl) benzoic acid ester derivatives of said formula 4 is carried out using the same method which esterified the compound of said formula 3. And the method is presented below.

The esterification is carried out at −5~100° C., preferably at 40~50° C. An alcohol compound is used as a reacting material and solvent. Even though there is no restriction for the content of the alcohol compound, it is rather economical to add 1~10 equivalent, preferably 1.2~1.5 equivalent by mole ratio in proportion to o-(chloromethyl)benzoic chloride expressed by the formula 3.

According to the invention, the esterification is mildly carried out in the absence of a base. If alkylamine (e.g., trimethylamine, trietlhylamine, triisopropylamine) as tertiary amines or aromatic amines such as pyridine is added as a base, the desired compound expressed by the above formula 4 may be obtained under a mild condition with a high yield. When a base is added for esterification, the reaction temperature is maintained at 0~20° C. more preferably at 5~10° C.

After the esterification is completed under the above condition, the desired compounds expressed by the formula 4 is recovered in a common purification procedure; for example, the reacting mixture is washed with water and subject to a fractional distillation under reduced pressure; or without washing process, the reaction mixture is distillated fractionally under reduced pressure.

Further, the method for preparing a compound expressed by the formula 5, so obtained from the reaction between a compound expressed by the formula 4 and sulfonic acid salt, is presented below.

The reaction between a compound expressed by the formula 4 and sulfonic acid salt is carried out at 30~90° C., preferably at 40~60° C. Thiosulfonic acid salt $[M_2(S_2O_3)]$ is added in the molar ratio of 1.0~2.0 equivalent to a compound expressed by formula 4, preferably in the molar ratio of 1.0~1.2 equivalent. Further, the method for preparing o-(carboalkoxy)phenylmethanesulfonyl chloride derivatives expressed by the formula 1 as a desired product, so obtained from the reaction via chlorination of o-(carboalkoxy) phenylmethanethiosulfonic acid salt, is presented below.

The chlorination is carried out at 0~20° C. in a common chlorination procedure using a chlorine gas($Cl_2$) or chlorination reagent, and it is preferred to perform the reaction at 5~10° C. using chlorine gas($Cl_2$).

The amount of chlorine is in the molar ratio of 3 equivalent or its excess. Further, it is preferred to use water or acetic acid as chlorination solvent and its concurrent use is possible.

After the chlorination is completed, the remaining chlorine gas is removed and then, water is added to a reactor for dilution of the reacting solution. The solid product, so formed, is filtered off, thereby obtaining a desired compound expressed by the formula 1.

This invention is explained in more detail by the following examples but is not limited by these examples. Besides some processes for preparation of specific compounds, which are explained in following examples, however derivatives comprising in this invention can be composed to the skilled of this art.

Example 1

Synthesis of o-(chloromethyl)benzoyl Chloride

A mixture of phthalide 134 g(1 mol), $SOCl_2$ 95 ml(1.3 mol), $BF_3Et_2O$ 2.5 ml (0.02 mol) and benzyltriethylammonium chloride 4.5 g(0.02 mol) was placed in a double-neck 500 ml flask equipped with a thermometer and cooler. The mixture was stirred for 15 hours, while maintaining the interal temperature of reactor at 95~100° C. for reaction. After the reaction is completed, a fractional distillation under reduced pressure was made at the reactor equipped with a fractional distiller to afford 180 g of a desired compound (yield 95%).
Boiling point: 75~80° C.(1 mm Hg)

Example 2

Synthesis of 4-chlorobutyryl Chloride

A mixture of $SOCl_2$ 11.42 ml, $BF_3Et_2O$ 0.29 ml and benzyltriethylammonium chloride 0.55 g was added to γ-butyrolactone 10 g in a reactor. The mixture was stirred for 4 hours, while maintaining the interal temperature of reactor at 90~95° C. for reaction. After the reaction is completed, a fractional distillation under reduced pressure was made to afford 11.6 g of a desired compound (yield: 70%).
Boiling point: 173~174° C.(760 mm Hg)

Example 3

Synthesis of o-(chloromethyl)benzoic Acid Methyl Ester 180 g of o-(chloromethyl)benzoyl chloride was placed in a double-neck 500 ml flask equipped with a thermometer, cooler and dropping funnel. While maintaining the internal temperature of a reactor at 40~50° C., 50 ml of methanol was added dropwise. After all amounts of methanol were infused, the reacting mixture was stirred for 10 hours, while maintaining the internal temperature of a reactor at 40~50° C. After a distillator was equipped, a fractional distillation under reduced pressure was made to afford 165 g of desired compound (yield 94%) as oil.
Boiling point: 77~80° C. (1 mm Hg)
$^1H$—NMR($CDCl_3$): δ 3.9(s, 3H), 5.02(s, 2H), 7.31~7.56(m, 3H), 7.96(d, 1H, J=8 Hz)

Example 4

Synthesis of o-(chloromethyl)benzoic Acid Methyl Ester

To a double-neck 500 ml flask equipped with a cooler, thermometer and dropping funnel was added 180 g of o-(chloromethyl)benzoic acid chloride dissolved in 1,000 ml of methylene chloride. The internal temperature was adjusted at 0° C., triethylamine(138 ml) was added and then 50 ml of methanol was added dropwise. After all amounts of methanol were infused, the reacting mixture was stirred for 10 hours, while maintaining the internal temperature of a reactor at 20~30° C.

The reaction mixture was acidified with 5% HCl solution (300 ml). The organic layer was separated, dried over magnesium sulfate, filtered, and concentrated. The residue, so formed, was subjected to fractional distillation under reduced pressure to afford 155 g of desired compound (yield 89%) as oil.

Example 5

Synthesis of o-(chloromethyl)benzoic Acid Ethyl Ester

To a double-neck 500 ml flask equipped with cooler, thermometer and dropping funnel was added 180 g of o-(chloromethyl)benzoic acid chloride, and then 60 ml of ethanol was further added dropwise, while maintaining the internal temperature of reactor at 40~50° C. After all amounts of methanol were infused, the reacting mixture was stirred for 10 hours, while maintaining the internal temperature of a reactor at 40~50° C. After a distiller was equipped immediately, the residue was subjected to fractional distillation under reduced pressure to afford 179 g of desired compound (yield 90%) as oil.
Boiling point: 79~82° C.(1.1 mm Hg)
$^1H$—NMR($CDCl_3$): δ 1.4(t, 3H, J=8 Hz), 4.38(q, 2H, J=8 Hz), 5.02(s, 2H), 7.32~7.55(m, 3H), 7.96(d, 1H, J=8 Hz)

Example 6

Synthesis of o-(chloromethyl)benzoic Acid 2-chloroethyl Ester 180 g of o-(chloromethyl)benzoic acid chloride was placed in a double-neck 500 ml flask equipped with a cooler, thermometer and dropping funnel. 50 ml of 2-chloroethanol was added dropwisely, while maintaining the internal temperature of reactor at 40~50° C. After all amounts of 2-chloroethanol were infused, the reacting solution was stirred for 10 hours, while maintaining the internal temperature of reactor at 40~50° C. The residue was subjected to fractional distillation under reduced pressure at the reactor equipped with a fractional distiller to afford 165 g of desired compound (yield 94%) as oil.
Boiling point: 88~92° C.(1.1 mm Hg)
$^1$H—NMR(CDCl$_3$): δ 3.83(t, 2H, J=5.5 Hz), 4.59(t, 2H, J=5.5 Hz), 5.02(s, 2H), 7.36~7.58(m, 3H), 8.01(d, 1H, J=8 Hz)

Example 7

Synthesis of o-(carbomethoxy) phenylmethanesulfonyl Chloride

A mixture of water (50 ml) and 29.5 g of sodium thiosulfate pentahydrate was added to o-(chloromethyl) benzoic acid methyl ester 20 g, and stirred for 5 hours at 50~55° C. 300 ml of acetic acid was added and then excess of chlorine gas for 3 hours was infused, while maintaining the internal temperature of reactor at 5~10° C. The reaction mixture was further stirred for 1 hour at the same temperature. Excess of chlorine gas was removed via infusion of nitrogen gas and with the addition of ice water (300 ml), stirred for 30 minutes. A solid, so formed, was filtered with a cold water and dried to afford 22.4 g of desired compound (yield 83%) as a white solid.
Melting point: 85~86° C.
$^1$H—NMR(CDCl$_3$): δ 3.95(s, 3H), 5.67(s, 2H), 7.51~7.68 (m, 3H), 8.07~8.16(m, 1H)

Example 8

Synthesis of o-(2-ethoxycarbonyl) phenylmethanesulfonyl chloride

The reaction was carried out in the same manner as Example 7, using 20 g of o-(chloromethyl)benzoic acid ethyl ester instead of o-(chloromethyl)benzoic acid methyl ester to afford 21.5 g of desired compound (yield 81%) as a white solid.
Melting point: 63~64° C.
$^1$H—NMR(CDCl$_3$): δ 1.4(t, 3H, J=8 Hz), 4.4(q, 2H, J=8 Hz), 5.66(s, 2H), 7.51~7.68(m, 3H), 8.07~8.15(m, 1H)

Example 9

Synthesis of o-(2-chloroethoxycarbonyl) phenylmethanesulfonyl chloride

The reaction was carried out in the same manner as Example 7, using 20 g of o-(chloromethyl)benzoic acid 2-chloroethyl ester instead of o-(chloromethyl)benzoic acid ethyl ester to afford 20.5 g of desired compound (yield 80%) as a white solid.
Melting point: 66~67° C.
$^1$H—NMR(CDCl$_3$): δ 3.83(t, 2H, J=5.5 Hz), 4.59(t, 2H, J=5.5 Hz), 5.4(s, 2H), 7.52~7.68(m, 3H), 8.15(d, 1H, J=8 Hz)

What is claimed is:
1. A process for preparing an o-(carboalkoxy) phenylmethanesulfonyl chloride derivative of formula (1), comprising the steps:
 (a) reacting a lactone compound of formula (2) with thionyl chloride in the presence of a Lewis acid and a quaternary-ammonium salt catalyst to prepare an o-(chloromethyl)benzoic chloride of formula (3);
 (b) esterifying said o-(chloromethyl)benzoic chloride of formula (3) in an alcohol compound as a reacting material and solvent to prepare an o-(chloromethyl) benzoic acid ester of formula(4);
 (c) reacting said o-(chloromethyl) benzoic acid ester of formula(4) with a thiosulfonic acid salt to prepare an o-(carboalkoxy)phenylmethanethiosulfonic acid salt of formula (5); and
 (d) chlorinating said o-(carboalkoxy) phenylmethanethiosulfonic acid salt of formula (5) to prepare an o-(carboalkoxy)phenylmethanesulfonyl chloride derivative of formula(1);
wherein said chemical formulae are

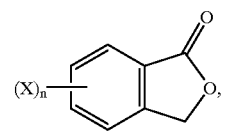
(2)

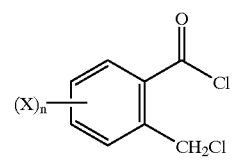
(3)

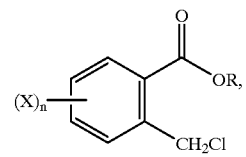
(4)

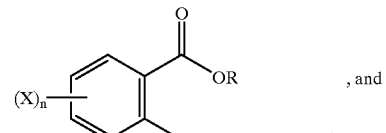
(5)
, and

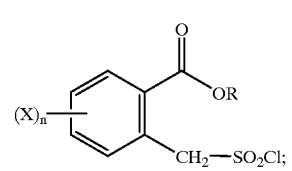
(1)

wherein:
X is chosen from a hydrogen atom, halogen atoms, $C_1$ to $C_6$ alkyl groups, $C_1$ to $C_6$ haloalkyl groups, $C_1$ to $C_6$ alkoxy groups, $C_1$ to $C_6$ alkoxycarbonyl groups, a nitro group, and a phenyl group;
R is chosen from $C_1$ to $C_6$ alkyl groups, $C_1$ to $C_6$ haloalkyl groups, and $C_3$ to $C_6$ cycloalkyl groups;
n is chosen from integers ranging from 1 to 4.
2. The process according to claim 1, wherein said reacting of step (a) is carried out at a temperature ranging from 90 to 100° C.
3. The process according to claim 1 or 2, wherein said reacting of step (a) is carried out in the presence of a solvent.
4. The process according to claim 1, wherein said Lewis acid catalyst is chosen from MgCl$_2$, MgBr$_2$, SnCl$_2$, SnCl$_4$, TiCl$_4$, AlCl$_3$, FeCl$_3$, BF$_3$•Et$_2$O, BCl$_3$, B(OEt)$_3$, B(OMe)$_3$, and B(OiPr)$_3$.
5. The process according to claim 1 or 4, wherein said Lewis acid catalyst is chosen from BF$_3$•Et$_2$O, B(OEt)$_3$, B(OMe)$_3$, and B(OiPr)$_3$.

6. The process according to claim 1, wherein said quaternary-ammonium salt is chosen from tetramethylammonium chloride, tetraethylammonium chloride, tetrabutylammonium chloride, benzyltrimethylammonium chloride, benzyltriethylammonium chloride, and benzyltributylammonium chloride.

7. The process according to claim 1, wherein, in said step (b), said alcohol compound is methanol.

8. The process according to claim 1, wherein said esterfying of step (b) is carried out in the presence of a base chosen from trimethylamine, triethylamine, triisopropylamine, and pyridine.

9. The process according to claim 1, wherein, in said step (c), said thiosulfonic acid salt is $M_2(S_2O_3)$, wherein M is an alkali metal.

10. The process according to claim 1, wherein said chlorinating of step (d) is carried out in the presence of water, acetic acid, or a mixture thereof.

11. The process according to claim 1 or 10, wherein said chlorinating of step (d) is carried out at a temperature ranging from 0 to 20° C.

12. The process according to claim 1 or 10, wherein in said chlorinating of step (d), the chlorinating reagent is chlorine gas.

13. The process according to claim 11, wherein in said chlorinating of step (d), the chlorinating reagent is chlorine gas.

* * * * *